United States Patent [19]

Mehrotra

[11] Patent Number: 5,047,339

[45] Date of Patent: Sep. 10, 1991

[54] RECOVERY OF POLYETHER ANTIBIOTIC MATERIAL

[75] Inventor: Vikram P. Mehrotra, Terre Haute, Ind.

[73] Assignee: International Minerals & Chemical Corp, Northbrook, Ill.

[21] Appl. No.: 854,106

[22] Filed: Apr. 21, 1986

[51] Int. Cl.$^5$ .................... C12P 17/16; C12P 17/18; C12N 1/38; C07D 407/00

[52] U.S. Cl. .................... 435/118; 435/119; 435/886; 435/244; 549/414

[58] Field of Search .............. 435/119, 118, 123, 244, 435/271, 253.5; 424/123; 549/414

[56] References Cited

U.S. PATENT DOCUMENTS

| | | | |
|---|---|---|---|
| 968,206 | 8/1910 | Strom | 210/43 |
| 2,289,669 | 7/1942 | Maxton | 210/43 |
| 2,361,283 | 10/1944 | Good | 196/39 |
| 2,438,244 | 3/1948 | Biazzi | 252/349 |
| 2,611,488 | 9/1952 | Resan | 210/43 |
| 3,471,401 | 10/1969 | Huval | 210/23 |
| 4,033,823 | 7/1977 | Liu | 195/80 |
| 4,395,491 | 7/1983 | Hohl et al. | 435/262 |

OTHER PUBLICATIONS

Stark et al, Antimicrob. Agents and Chemotherapy, 1967, pp. 353–358.

V. P. Mehrotra et al., *International Journal of Mineral Processing*, 11 (1983) 175–201.

*Primary Examiner*—Douglas W. Robinson
*Assistant Examiner*—Irene Marx
*Attorney, Agent, or Firm*—Wendell R. Guffey; Thomas L. Farquer

[57] ABSTRACT

An aqueous medium having dispersed therein hydrophobic, polyether antibiotic-containing droplets, is mixed to cause the droplets to collide with each other and coalesce to form agglomerates which are separable from the medium.

12 Claims, No Drawings

RECOVERY OF POLYETHER ANTIBIOTIC MATERIAL

BACKGROUND OF THE INVENTION

1. Field of the Invention

The present invention relates to preparation of a polyether antibiotic-containing material.

2. Description of the Background Art

Polyether antibiotics can be generally characterized as carboxylic acid ionophores which can be produced by culturing Streptomyces type microorganisms. These polyether antibiotics have a basic structure generally consisting essentially of the elements oxygen, hydrogen and carbon and possibly nitrogen and have a molecular weight in the range of about 300 to about 1800, most often from about 400 to about 1200. They have low solubility in water, are generally soluble in low molecular weight alcohols, ethers and ketones, and have at least one, and usually one or two, carboxylic acid groups. A generally comprehensive review of this class of antibiotics is set forth in Westley, *Adv. Appl. Microbiology*, 22:177-223 (1977). At least twenty different polyether antibiotics were known at the time the Westley article was written. Since then, additional polyether antibiotics have been discovered.

In the previously noted publication, Westley classified the known polyether antibiotics into four separate classes based on ability of the particular antibiotic to effect the transport of divalent cations and based on the chemical structure of the particular antibiotic. Using these criteria, Westley defined class 1a as those polyether antibiotics which are monovalent polyether antibiotics. In addition, the polyether antibiotics of this class have a generally linear configuration, i.e., the carboxylic portion of the polyether molecule is attached either directly or indirectly to a terminal ring structure. They generally include from about four to about six tetrahydropyran and/or -furan structures and up to six total ring structures. Included in class 1a are the polyether antibiotics monensin, laidlomycin, nigericin, grisorixin, salinomycin, narasin, lonomycin, X-206, SY-1, noboritomycins A & B, mutalomycin, and alborixin.

Class 1b of the polyether antibiotics are defined by Westley as monovalent monoglycoside polyether antibiotics. These polyether antibiotics, as the class name suggests, include a glycoside type structure, more specifically, a 2,3,6-trideoxy-4-0-methyl-D-erythrohexapyranose moiety, which is attached to the polyether molecule such that a non-linear type molecule is formed, i.e., the carboxylic portion of the polyether molecule is attached either directly or indirectly to a non-terminal ring structure or the molecule has a side chain ring structure, e.g., a 2,3,6-trideoxy-4-O-methyl-D-erythrohexapyranose moiety. Generally, the polyether antibiotics of this class contain about six or seven tetrahydropyran and/or -furan structures. Included within class 1b are the polyether antibiotics septamycin, dianemycin, A-204, lenoremycin, carriomycin and etheromycin.

Class 2a as defined by Westley is directed to divalent polyether antibiotics. These antibiotics have a generally linear configuration, may contain from about two to about three tetrahydropyran and/or -furan structures, up to about three total ring structures and no nitrogen atoms. Included within class 2a are the antibiotics lasalocid and lysocellin.

Westley's class 2b of polyether antibiotics is directed to divalent pyrrole ethers and thus, in contrast to the antibiotics of the other classes, the class 2b antibiotics contain one or more nitrogen atoms. Included within class 2b are the polyether antibiotics X-14547, and A-23187 also known as calcimycin.

Polyether antibiotics are generally produced by fermenting a nutrient-containing liquid fermentation medium or broth inoculated with a microorganism capable of producing the desired antibiotic. Suitable liquid fermentation media are generally aqueous dispersions containing sources of assimilable nitrogen and carbon as is known in the art. The fermentation media can also contain a variety of optional ingredients, if desired, such as for example, pH adjustment agents, buffers, trace minerals, antifoam agents, and the like.

Known methods for recovering polyether antibiotics from fermentation broths generally involve complicated and expensive multi-stage solvent extractions and related filtration, chromatography, concentration, and crystallization operations. For example, the procedure to isolate and purify lysocellin first described by Ebata et al. used acetone, n-butanol and methanol (Ebata et al., *J. Antibiotics*, 28:118-121 (1975)). U.S. Pat. No. 4,033,823 describes an extraction process involving ethyl acetate, acetonitrile, hexane and methanol for recovering lysocellin. Commonly owned U.S. Pat. No. 4,478,935 describes various purified manganese-containing antibiotic complexes extracted from the dried biomass using suitable organic solvents followed by crystallization or precipitation of the complexes. All of these processes follow a rather standard approach in which fermentation broths are subjected to organic solvent extraction to recover the polyether antibiotics. The isolation and purification of polyether antibiotics using extraction methods have been extensively reviewed in Hamill et al., "Polyether Antibiotics" pp. 479-520, *J. Chromatogr. Lib.*, Vol. 15. Antibiotics: Isolation, Separation, and Purification, ed. by Weinstein, M.J. and Wagman, G.H. (1978).

There remains a need in the art for a method for preparing polyether antibiotic material without the need for complicated and expensive multi-stage solvent extractions and related filtration, chromatography, concentration and crystallization operations and the like.

SUMMARY OF THE INVENTION

In accordance with the present invention, a method for recovering a polyether antibiotic material comprises mixing an aqueous medium having hydrophobic droplets dispersed therein to cause the droplets to collide with each other and coalesce to form agglomerates which are separable from the medium, the hydrophobic droplets comprising polyether antibiotic and a hydrophobic material which is capable of adsorbing on the polyether antibiotic without degrading the polyether antibiotic. The agglomerates then are separated from the medium.

DETAILED DESCRIPTION OF THE PREFERRED EMBODIMENTS

Polyether antibiotic material generally is produced by fermenting a polyether antibiotic-producing microorganism which secretes a lipophilic polyether antibiotic into an aqueous medium. Polyether antibiotic-producing microorganisms, such as a lysocellin-producing strain of *Streptomyces asoensis*, are cultivated in a generally aqueous fermentation broth (sometimes referred to herein as culture medium or nutrient medium). Although the invention is specifically described herein with respect to the preparation of a lysocellin material, it is to be understood that the invention is also applicable to other polyether antibiotics.

For growth of the microorganism and production of polyether antibiotic, the fermentation broth contains assimilable sources of carbon and nitrogen, and may contain trace elements and other optional ingredients, as is known in the art. In accordance with one embodiment, lipid contained in agglomerates according to this invention is an assimilable source of carbon for the microorganism.

Examples of lipids which are suitable for use according to this invention include substantially liquid triglyceride oils, free fatty acids, and phospholipids such as lecithin.

An assimilable source of nitrogen is also provided in the culture medium. Suitable sources of nitrogen include yeast, yeast-derived products, enzyme-hydrolyzed caseine, peptones, cornmeal, soybean meal, cottonseed meal, amino acids such as glutamic acid, and the like.

Nutrient inorganic salts can also be incorporated in the culture medium such as soluble salts capable of yielding sodium, magnesium, calcium, ammonium, chloride, carbonate, sulfate, nitrate, and like ions. Essential trace elements necessary for the growth and development of the microorganism should also be included in the culture medium. Such trace elements commonly occur as impurities in other constituents of the medium in amounts sufficient to meet the growth requirements of the organism.

Polyether antibiotics are produced by growing the polyether antibiotic producing microorganism in an aerated, agitated, submerged culture with the pH of the broth adjusted to about neutral, i.e., from about 6.5 to about 7.5. Fermentation can generally be carried out at slightly elevated temperatures, e.g., between about 25° C. and 35° C. Incubation of the broth can be carried out for a period of several days, e.g., from about 4 to 12 days or longer if it is economically advantageous to do so.

It may be necessary to add small amounts (i.e., 0.2 ml/l) of an anti-foam agent such as polypropylene glycol to large-scale fermentation media if foaming becomes a problem. Excessive foaming may occur, for example, when fatty acids are added initially to the fermentation broth as the principal carbon source.

In one embodiment, lipid for forming agglomerates with polyether antibiotic is comprised of triglycerides, free fatty acids, salts thereof, or mixtures thereof. Suitable triglycerides include soybean oil, safflower oil, cottonseed oil, sesame oil, olive oil, rape oil, peanut oil, corn oil, sunflower oil and like vegetable oils, cod oil and like fish oils, and lard and like animal-fat-and-oils. Vegetable oils are a preferred triglyceride source, with soybean oil being particularly preferred.

The free fatty acids which may be used according to the present invention include saturated fatty acids such as lauric acid, myristic acid, palmitic acid, stearic acid, arachidic acid, lignoceric acid and the like, and unsaturated fatty acids such as palmitoleic acid, oleic acid, linoleic acid, linolenic acid, arachidonic acid and the like. Unsaturated fatty acids are preferable for use according to the present invention, with oleic acid being most preferred.

In a particularly preferred embodiment, the fermentation broth contains as a principal carbon source a mixture of free fatty acids and triglycerides, most preferably a mixture of oleic acid and soybean oil. According to this embodiment, the respective ratio by weight of oleic acid to soybean oil during at least a portion of fermentation is from about 4:1 to about 2:3.

Free fatty acids, such as oleic acid, are much more quickly metabolized during fermentation as compared to triglyceride oils, but are generally quite toxic to microorganisms except at low concentrations. Free fatty acids can thus advantageously be used to obtain higher antibiotic yields or titers by continuously feeding low concentrations of free fatty acids to the broth during fermentation at about a rate at which the free fatty acids are metabolized. If free fatty acids are used alone during fermentation as principal carbon source and are depleted at the end of fermentation, accruing crystals of polyether antibiotic are freely suspended in the fermentation broth and do not form agglomerates. Addition of at least a small amount of triglycerides with free fatty acids during fermentation, which is preferably fed on a continuous basis to the on-going fermentation, can result in sufficient triglycerides being present in the broth to facilitate the formation of agglomerates.

According to one embodiment, growth of a lysocellin-producing strain of the genus Streptomyces is established in a generally aqueous fermentation broth initially containing as a principal carbon source about 8% by weight or less lipids (preferably 3% or less). The broth is fermented to produce hydrophobic lipid/lysocellin droplets dispersed in the medium. Lipid can be fed into the broth as fermentation proceeds, but is kept at a level of about 8% by weight or lower (preferably 3% or lower).

After suitable lysocellin titers are achieved (e.g., after up to about 12 days of fermentation) the aqueous broth is mixed (e.g., by stirring or shaking) to cause the droplets to collide with each other and coalesce to form agglomerates which are separable from the medium. If desired, additional oil or water can be added to the medium to facilitate agglomerate formation. For agglomerates to form, the lysocellin must be substantially coated with lipid. However, the viscosity of the medium must be sufficiently low to permit enough movement of the droplets to collide and coalesce. While adding additional water is a simple means of lowering viscosity of the medium, other suitable means could be used. The agglomerates either settle to the bottom or float (depending on density) and can either be scraped from the surface of the broth or screened (e.g., with U.S. standard 20-35 mesh screen). If desired, air can be bubbled through the mixture to float agglomerates to the surface where they can be removed by surface scraping methods. Agglomerates generally form in a matter of minutes or hours during mixing, sometimes after only 2-5 minutes of mixing, and typically will contain about 25-60% by weight lipid and about 40-75% by weight lysocellin. The amount of mixing or agitation required to form agglomerates must be sufficient to cause collision and coalescence of the droplets, but less than an amount which causes disintegration of droplets or agglomerates due to sheering.

Agglomerates produced according to the present invention are particularly useful as providing means for obtaining very pure polyether antibiotic material in a relatively inexpensive manner. For recovery of the polyether antibiotic from the agglomerates, the agglomerates are added to an aqueous solution with base (e.g., 2% NaOH (aq)) to achieve and maintain a pH of from about 10 to about 12, in order to separate the lipid portion of the agglomerates and liberate the polyether antibiotic as an insoluble material. In order to facilitate rapid separation of the lipids from the polyether antibiotic present in the agglomerates, the solution containing agglomerates and NaOH is advantageously agitated to liberate the insoluble polyether antibiotic material from the agglomerates.

The insoluble polyether antibiotic material then is isolated, e.g., by centrifugation or filtration, from the aqueous soap solution. This process has been utilized to obtain lysocellin purities for dried solids obtained directly from the soap solution in the range of from about 70-99%. Optionally, additional hexane washes can be utilized to improve the purities to 95-99% without significantly decreasing recoveries, since the solids from the NaOH solution generally contain more than 90% of the desired sodium salt of lysocellin which is essentially insoluble in hexanes. Additional sodium conversion is possible for the crude lysocellin crystals when mixed with caustic in methanol.

The present invention can be utilized to prepare a polyether antibiotic material of high purity without the need for complicated and expensive multi-stage solvent extractions and related filtration, chromatography, concentration and crystallization operations.

The invention is further illustrated by the following examples which is not intended to be limiting.

EXAMPLE I

Fermentation

Capsules of seed culture of a lysocellin-producing strain of S. Asoensis containing 1 ml of culture in glycerol are stored at −80° C. The content of one capsule is added to 80 ml first stage inoculum medium in a 500 ml Erlenmeyer flask. The medium contains (in wt. %) glycerol (2%), Bacto Peptone (1%), Bacto Meat Extract (1%), and tap water to volume. The flask is incubated on a rotary action shaker (~350 rpm) at 28° -30° C. for 48 hours (until satisfactory growth is established), and this seed is used immediately to inoculate second stage inoculum as follows.

2.5 Percent of the first stage inoculum is added to 100 ml second stage inoculum medium in each of several 500 ml Erlenmeyer flasks. The medium contains (by wt. %) soybean oil (2.5%), soybean flour (2.5%), $KH_2PO_4$ (0.15%), $K_2HPO_4$ (0.15%), and the trace elements $FeSO_4 \cdot 7H_2O$ (5 ppm), $MnSO_4 \cdot H_2O$ (1.5 ppm), $CoCl_2 \cdot 6H_2O$ (0.5 ppm), and distilled water. The flasks are incubated on rotary action shakers (~350 rpm) at 28° -30° C. for about 24 hours. The second stage inoculum is transferred immediately from shaker to fermenter.

In separate fermentations, 200 milliliters from 2 flasks of the second stage inoculum are used (~2% wt.) to inoculate a 20-liter sterilized fermenter containing (by wt. %) as "standard" principal medium soybean flour (4.5%), soybean oil (6.5%), $KH_2PO_4$ (.05%), $K_2HPO_4$ (0.15%), and $CoCl_2 \cdot 6H_2O$ (1 ppm). Hodag K-67 antifoam (about 0.1%) and tap water to about a 10 liter volume. The pH of the inoculated medium is about neutral and does not require any further pH adjustment.

The physical parameters for fermentations using a New Brunswick fermenter are as follows:

| | | |
|---|---|---|
| Medium, volume | 10,000 ml | |
| Air | 10 l/min | (5 l/min during first 16 hr) |
| PSI g | 4 | |
| Agitation | 2 impellers, 10.8 cm diam. | |
| RPM | 650 | |
| Temperature | 29-30° C. | |

After about 6 days fermentation, an additional 2% by weight soybean oil is added to the medium and fermentation is completed when lysocellin concentration reaches 8-18 g/l. The ferment appears brown with distinct yellow droplets.

EXAMPLE II

Agglomeration

A 50 g sample of ferment prepared generally as described in Example I was added to a 250 ml beaker with 10 g H2O. The contents of the beaker were agitated for two minutes with a Yamato laboratory stirrer model LR41D at 250 rpm with a four-blade impeller about two inches in diameter. Agglomerates formed after two minutes agitation, and were separated by pouring the slurry on a 20 mesh screen which retained the agglomerates and allowed liquid to pass through. Analysis of the agglomerates indicated the presence of about 41% by weight lysocellin in the agglomerates.

What is claimed is:

1. A method for recovering a polyether antibiotic material comprising:
    (a) mixing an aqueous medium having lipid droplets dispersed therein to cause the droplets to collide with each other and coalesce to form agglomerates which are separable from the medium, the lipid droplets comprising polyether antibiotic and a lipid material capable of adsorbing on said polyether antibiotic without degrading said polyether antibiotic; and
    (b) separating the agglomerates from the medium.

2. The method of claim 1 wherein the lipid droplets comprise about 25-60% by weight substantially liquid lipid and about 40-75% by weight polyether antibiotic.

3. The method of claim 2 wherein the lipid is added to the medium prior to or during mixing.

4. The method of claim 1 wherein the viscosity of the medium is reduced by addition of water to the medium prior to or during mixing.

5. The method of claim 2 wherein the lipid comprises triglycerides, fatty acids or mixtures thereof.

6. The method of claim 5 wherein the triglycerides comprise soybean oil and the fatty acids comprise oleic acid.

7. The method of claim 1 wherein the polyether antibiotic is lysocellin.

8. The method of claim 2 wherein the polyether antibiotic is lysocellin.

9. The method of claim 3 wherein the polyether antibiotic is lysocellin.

10. The method of claim 4 wherein the polyether antibiotic is lysocellin.

11. The method of claim 5 wherein the polyether antibiotic is lysocellin.

12. The method of claim 6 wherein the polyether antibiotic is lysocellin.

* * * * *